United States Patent [19]
Freudenberger et al.

[11] 4,096,156
[45] Jun. 20, 1978

[54] PROCESS FOR THE CATALYTIC MANUFACTURE OF γ-BUTYROLACTONE

[75] Inventors: Dieter Freudenberger, Hofheim, Taunus; Friedrich Wunder, Florsheim, Main; Hans Fernholz, Fischbach, Taunus, all of Germany

[73] Assignee: Hoechst Aktiengesellschaft, Frankfurt am Main, Germany

[21] Appl. No.: 744,320

[22] Filed: Nov. 23, 1976

[30] Foreign Application Priority Data
Nov. 29, 1975  Germany .............................. 2553761

[51] Int. Cl.$^2$ .......................................... C07D 307/32
[52] U.S. Cl. ................................................ 260/343.6
[58] Field of Search ..................................... 260/343.6

[56] References Cited
U.S. PATENT DOCUMENTS

| | | |
|---|---|---|
| 2,772,292 | 11/1956 | McShane et al. ................. 260/343.6 |
| 3,948,805 | 4/1976 | Michalcyzk ....................... 260/343.6 |
| 4,001,282 | 1/1977 | Miller ............................... 260/343.6 |

*Primary Examiner*—Norma S. Milestone
*Attorney, Agent, or Firm*—Curtis, Morris & Safford

[57] ABSTRACT

γ-butyrolactone, which is an important preliminary product for the preparation of butanediol-(1,4) and of pyrrolidone, is manufactured by catalytic hydrogenation of maleic acid, maleic acid anhydride, succinic acid, succinic acid anhydride, or fumaric acid, or of a mixture of two or more of these compounds, using a catalyst containing a mixture of an element of the VIII$^{th}$ subgroup of the periodic system of elements or of one of its compounds with an element of the I$^{st}$ subgroup of the periodic system of elements or of one of its compounds. The process is highly selective, and the yields of γ-butyrolactone are, therefore, excellent.

17 Claims, No Drawings

PROCESS FOR THE CATALYTIC MANUFACTURE OF γ-BUTYROLACTONE

The present invention relates to a process for the catalytic manufacture of γ-butyrolactone from maleic acid anhydride and maleic acid, as well as succinic acid anhydride, succinic acid, fumaric acid and/or mixtures of these compounds. γ-butyrolactone serves, for example, as preliminary product for the manufacture of butanediol-(1,4) and is also employed for the synthesis of pyrrolidone.

The manufacture of γ-butyrolactone is already known. In addition to a large number of previously known syntheses for producing γ-lactone from butanediol-(1,4), recently specific processes for production of γ-butyrolactone by catalytic hydrogenation of maleic acid anhydride and succinic acid anhydride, respectively, of their corresponding acids or, as well, of fumaric acid in the gaseous or liquid phase have been described.

While the hydrogenation in the gaseous phase is usually operated with copper-zinc-catalysts and throughout produces relatively small space/time yields, substantially more complicated multicomponent systems are described as catalysts for hydrogenations in the liquid phase. They comprise, in general, the elements nickel, molybdenum and rhenium. However, the descriptions include also cobalt, palladium, ruthenium, platinum, chromium as well as rhodium, zinc, barium, thallium, thorium, tungsten, iron, cadmium and manganese. A substantial disadvantage of these catalysts which are often fixed onto carriers of coal, $Al_2O_3$ or $SiO_2$ is their lack of resistance to acids, and their resultant unsuitability insufficient for a permanent industrial scale operation, especially e.g. to heavily acidic maleic acid or its anhydride.

Another particularly typical disadvantage of these known processes resides in the fact, that besides the formation of γ-butyrolactone, there are always formed considerable quantities of further reaction products such as n-butanol, n-propanol, n-butyric acid, propionic acid and especially tetrahydrofurane, tetrahydrofurane in many cases being the main product.

These disadvantages diminish considerably the profit at which these processes can be operated. Therefore, they are economically uninteresting as syntheses strictly for obtaining γ-butyrolactone.

A catalytic process for the manufacture of γ-butyrolactone has been found now, which allows production of γ-butyrolactone at a selectivity rate of almost 100% at practically quantitative conversion rates from maleic acid or from maleic acid anhydride, as well as from succinic acid, succinic acid anhydride and fumaric acid.

The present invention is therefore a process for the manufacture of γ-butyrolactone from maleic acid or from maleic acid anhydride or from succinic acid or from succinic acid anhydride or from fumaric acid, or from mixtures of these compounds, by catalytic hydrogenation, which comprises that maleic acid, maleic acid anhydride, succinic acid, succinic acid anhydride or fumaric acid or mixtures of these compounds are reacted with hydrogen in the presence of hydrogenation catalysts containing a mixture of an element of the $VIII^{th}$ subgroup of the periodic system of elements or of one of its compounds with an element of the $I^{st}$ subgroup or of one of its compounds.

The novel process, in comparison to the above-mentioned processes known hitherto, excels especially by a surprisingly high selectivity of the formation of γ-lactone, which is always considerably higher than 90 mol % and most often even reaches 99 mol %. This fact reduces to a minimum the production of undesirable accompanying or secondary products, especially of tetrahydrofurane. The process of the invention becomes thereby economically interesting and also extremely advantageous from a technological standpoint.

Especially surprising is the fact that the particularly high selectivity rate of the formation of γ-lactone from maleic acid anhydride, which was not observed previously to such an extent, is achieved in a very simple manner by combining elements of the $VIII^{th}$ subgroup with those of the $I^{st}$ subgroup, especially by adding silver or gold, or silver compounds or gold compounds, to palladium hydrogenation catalysts.

This effect is also unexpected insofar that neither silver nor gold have been described hitherto as catalysts for the hydrogenation of organic acids, but have been rather known as main components or co-components for oxidation catalysts.

The process of the present invention not only excels by its being technologically simple operation, but moreover by being of special economical interest, since the catalysts have excellent stability and may be employed easily for long-time use without any loss of activity, and may be recycled several times. The combination according to the present invention of elements of the $I^{st}$ subgroup of the periodic system of elements (especially gold and silver) or their compounds with those of the $VIII^{th}$ subgroup of the periodic system of elements (especially palladium) or their compounds, results in a surprisingly high stabilizing effect and extends significantly the life time of the catalysts. This factor is of essential importance for a permanent operation on a technological scale and is a reason for the superiority of the novel process as compared to the former ones.

The catalysts used for the novel process may contain the active components, e.g. palladium and silver or palladium and gold, but as well palladium, gold and silver, either as elements or as their compounds or as mixtures of both, optionally combined with carriers.

Accordingly, the manufacture of the catalysts may be carried out in such a way that suitable compounds are used directly, optionally on carriers, or that these compounds are reduced to a larger or minor extent, optionally to the elements.

Suitable compounds are, for example, oxides, oxide-hydrates, carbonates, nitrates, borides, carboxylates, such as acetates, propionates and butyrates, chelates of 1,3-diketo compounds, e.g. enolates such as acetylacetonates, benzoylacetonates and acetoacetic ester compounds. Especially suitable are carboxylates, carbonates, chelates of 1,3-diketo compounds, acetylacetonates, nitrates, oxides, oxide-hydrates and, e.g. for gold, aurates or acetoaurates.

For technical and economical reasons preference is given to the use e.g. of palladium as palladium-(II)-acetate or palladium-acetylacetonate, of silver as acetate or nitrate and of gold as gold-(II)-acetate or barium acetoaurate, all the more since these products are easily accessible or even commercially available. The catalysts which are employed in the novel process contain elements or compounds of elements of the $VIII^{th}$ subgroup as well as those of the $I^{st}$ subgroup of the periodic system of elements, including mixtures of elements of one group with compounds of elements of the other groups. From the I$^{st}$ subgroup silver and gold from the VIII$^{th}$ subgroup, and are especially suitable palladium, rhodium, platinum, iridium, ruthenium and osmium. Silver, gold and palladium are preferably employed.

The weight ratio of the elements of the VIII$^{th}$ subgroup to those of the I$^{st}$ subgroup of the periodic system of elements keeps approximately within 99:1 and 1:99, preferably within 10:1 and 1:10, calculated on the elements.

In general, the catalysts are used in the process according to the invention in the form of powders. However, they may also be used as pellets or possibly mixed with inert carrier material.

Suitable carriers may be, for example: silicon dioxide, diatomaceous earth, kieselguhr, titanium dioxide, silicic dioxide-aluminum oxide, coal, thorium oxide, zirconium oxide, silicic carbide, spinels and aluminum oxides. Preference is given to the use of such carriers which have relatively small specific surface areas, e.g. kieselguhr having a surface area of 0.1–10 m$^2$/g.

In the case where catalysts on carriers or catalysts blended with inert materials are used, the proportion of the catalytically active substances, i.e. of the elements or their compounds, varies in general from about 0.1 to 50 weight %, calculated on the total mass of the catalyst. Generally speaking, the quantity of the inert materials (carriers) thus varies between 99.9 and 50 weight % of the total mass of the catalyst.

As a result, the catalysts may be present either as elements or as their compounds or as mixtures of both, optionally combined with carriers. Therefore, their manufacture or preliminary treatment may also be carried out by various methods.

As an example, palladium-silver-catalysts may be prepared in general by applying onto a carrier — either by immersion or suspension of this carrier or by spraying on — e.g. a solution of a palladium carboxylate, or a solution of a compound such as palladium oxidehydrate which is subsequently converted carboxylic acids to palladium carboxylate, of palladium nitrate, of palladium oxycarbonate or of a salt of a 1,3-diketo compound such as acetoacetic ester or acetylacetone in an anhydrous or aqueous carboxylic acid together with silver acetylacetonate, silver nitrate or with a compound which converts to a silver carboxylate in the presence of a carboxylic acid.

The carboxylic acid is then removed by drying at elevated temperatures, preferably at temperatures from 40° to 100° C, in a vacuum or under normal pressure. The catalyst may now be inserted directly, preferably, however, it is first treated with reducing agents in the gaseous or liquid phase at temperatures from 15° to 250° C.

The manufacture e.g. of palladium-gold-catalysts or of palladium-gold-silver-catalysts is carried out analogously. In this case the gold proportion is preferably introduced in the form of gold acetate or barium aurate or barium acetoaurate. The barium which has been introduced with the gold may either remain in the catalyst material or it may also be removed, preferably after the reduction of the catalyst, by a suitable treatment, e.g. by a washing step with water or carboxylic acids. Particularly in this case the obtained catalysts resist to dissolution, especially by maleic acid.

Especially suitable carboxylic acids are all those aliphatic carboxylic acids which contain in the molecule from 2 to 10 carbon atoms and are liquid under normal conditions and vaporizable without dissociation in vacuo. Preference is given to acetic acid, propionic acid or butyric acid, but especially to acetic acid.

The solutions of the compounds which are used for the manufacture of the catalysts, e.g. the solution of a palladium salt and of a suitable gold compound and/or silver compound, may be applied onto the carriers separately. It is, however, advantageous to dissolve the palladium compound and the gold compound or silver compound together in a carboxylic acid. It is also possible to apply first onto the carrier one of the aforesaid palladium compounds and to spread thereon subsequently the solution of a gold compound and/or silver compound in a carboxylic acid. The carriers may have the form of a powder or may be shaped structures, e.g. granules, pellets, tablets, extruded pieces, saddles, rings or honeycomb tubes.

Reducing the catalysts may be carried out in the liquid phase, e.g. with hydrazine hydrate. More advantageous, however, is reducing at higher temperatures, e.g. of from 100° to 200° C, in the gaseous phase with reducing vapors or gases such as hydrogen, methanol, formaldehyde, ethylene, propylene or butenes, either diluted or undiluted. Especially favorable results have been obtained by strongly diluting at the beginning with inert gases such as nitrogen, carbon dioxide or rare gases and by a concentration of the reducing agent which increases with progressing reduction, so that for example the reduction is terminated in pure hydrogen. The reducing step may be carried out either in a separate device or in the same apparatus which is employed for the conversion of maleic acid anhydride, of maleic acid, or of succinic acid, succinic acid anhydride, fumaric acid and/or of their mixtures to γ-butyrolactone.

The catalysts may be pyrophoric. In this case they have to be treated accordingly. Especially advantageous is a reduction of the catalyst and the subsequent conversion e.g. of maleic acid and/or of the anhydride in one and the same apparatus.

In order to obtain the best possible results from the process according to the invention, the hydrogenolysis of the initial products, e.g. of maleic acid anhydride, is carried out in general at elevated pressures and elevated temperatures. Generally, the reaction temperatures vary within 50° to 300° C, preferably within the range of 150° to 250° C. The reaction pressure varies generally between 50 and 500 bars, preferably within the range of 100 to 350 bars.

The hydrogen which is used for the hydrogenolysis of maleic acid anhydride, of maleic acid, of succinic acid, of succinic acid anhydride, of fumaric acid or of their mixtures, is employed in general in quite important stoechiometric excess quantities. Hydrogen, not having participated in the reaction, can be recycled into the reaction as circulating gas. The reaction can be carried out either continuously or discontinuously. Hydrogen is most often used in a technically pure quality, but, additions of inert gases such as nitrogen do not influence detrimentally the course of the reaction.

Generally, the reaction time of the process according to the invention varies from 5 minutes to 8 hours. For a process operated discontinuously in an autoclave, the reaction time ranges e.g. from about 3 to 6 hours.

Pulverulent catalysts may be filtered off or evacuated by centrifugation after termination of the process for being re-used without any substantial losses in activity.

When operating continuously, e.g. in the trickling phase, catalysts are most often used as pellets or applied onto carriers.

For putting to practice the reaction, there may be used inert solvents known for hydrogenations, such as dioxane, tetrahydropyrane or further cyclic or open-chain ethers, e.g. tetrahydrofurane or diethyl ether, or as well the very reaction product, i.e. γ-butyrolactone.

Suitable solvents are also polyalkylene glycol dialkyl ethers, e.g. tetramethylene glycol dibutyl ether, tetramethylene glycol dipentyl ether, tetraethylene glycol dimethyl ether, tetraethylene glycol diethyl ether and diethylene glycol dibutyl ether or mixtures of these or further solvents, such as γ-butyrolactone. Especially good results have been obtained with such solvents having boiling points above 215° C owing to a technical facilitation of the continuous work-up of the reaction mixture (distillation). Preferred solvents are dioxane and tetrahydrofurane.

The initial solution contains maleic acid, maleic acid anhydride, succinic acid, succinic acid anhydride, fumaric acid and/or their mixtures in an amount of, in general, from 5 to 60 %, when solvents are also used as co-components. Good results have been obtained, for example, by using a 20 to 40 % solution of maleic acid anhydride in 1,4-dioxane, tetrahydrofurane, and also in γ-butyrolactone. As far as maleic acid is concerned, water or aqueous mixtures are also suitable solvents. Generally, the catalyst quantity necessary for hydrogenation, varies from 0.5 to 25 weight %, calculated on the quantity of reactants used for hydrogenolysis, e.g. of the quantity of maleic acid anhydride or maleic acid. Preferably the employed quantity of catalyst amounts to from 5 to 15 weight % and especially from 8 to 12 weight %.

Suitable initial materials may be maleic acid anhydride as well as maleic acid, also succinic acid, succinic acid anhydride, fumaric acid and also random mixtures of these initial substances, optionally while using inert solvents as co-components.

Especially economically interesting and therefore a preferred initial material is maleic acid anhydride.

The reaction mixtures are worked-up and the γ-butyrolactone isolated, in general, by fractionating distillation.

Among the various processing methods for carrying out the hydrogenolysis according to the invention, the following method has brought about especially good results e.g. for the discontinuous manufacture of γ-butyrolactone.

A solution of maleic acid anhydride in 1,4-dioxane is introduced into a high-pressure-autoclave together with the catalyst, hydrogen is forced in and the reaction mixture heated. After termination of the reaction, the reaction mixture is cooled, the catalyst separated and the mixture subjected to fractionating distillation.

The following examples illustrate the invention:

EXAMPLE 1

15 g of palladium-(II)-acetate are dissolved in 400 ml of acetic acid at 70° C. To this solution is added a solution of 5 g of silver nitrate in 80 ml of water and 50 g of kieselguhr are added subsequently. While stirring, e.g. in a rotation evaporator, evaporation to dryness is carried out in vacuo at 60° to 70° C and the result reduced at 200° C under a hydrogen atmosphere.

5 g of the thus prepared catalyst which contains 11.7 % of palladium and 5.2 % of silver as metals, are introduced into a 0.5 liter shaking autoclave with magnetic type lifting agitator together with 49 g of maleic acid anhydride and 100 ml of dioxane.

Hydrogen is forced in until a pressure of 210 bars is reached, then heating is carried out up to 225° C during 40 to 60 minutes. The reaction is interrupted after 4 to 5 hours. After a quick cooling step and after filtering off the catalyst under a carbon dioxide atmosphere, 150.1 g of a reaction solution clear as water is obtained, which contains 28.4 % (42.5 g) of γ-butyrolactone, corresponding to a yield of 99.1 mol %. Tetrahydrofurane, n-butanol and butane-diol-(1,4) can be detected by gas chromatography only in traces of less than 0.1 %.

EXAMPLE 2

15 g of palladium-(II)-acetate are dissolved at 70° C in 400 ml of acetic acid and 6.4 g of barium acetoaurate, dissolved at 70° C in 100 ml of acetic acid, are added. To this solution are added 50 g of kieselguhr, and then it is evaporated to dryness in vacuo at 60° to 70° C while stirring. The residue is reduced at 200° C for about 2 hours under a hydrogen atmosphere.

0.5 mol of maleic acid anhydride (49 g) are dissolved in 100 ml of dioxane. The solution is introduced into a one-liter-shaking autoclave together with 5 g of the pulverulent kieselguhr-catalyst which contains 11.8 % of palladium and 4.2 % of gold as metals and 1.4 % of barium as acetate. Hydrogen is forced in until a pressure of 215 bars is reached and the temperature is quickly brought up to 230° C. The reaction is interrupted after about 5 hours and the reaction mixture submitted to quick cooling. After having separated the catalyst, 149.9 g of a colorless reaction solution clear as water which contains 28.6 % of γ-butyrolactone (42.6 g), corresponding to a yield of 99.2 mol %, are obtained. Besides γ-butyrolactone and the solvent there may only be detected water and gaschromatographic traces (0.1 %) of n-butanol, butane-diol-(1,4) and tetrahydrofurane. The residual acid content is also situated below 0.1 %.

EXAMPLE 3

15 g of palladium-(II)-acetate and 3.2 g of barium acetoaurate are dissolved at 70° C in 400 ml of acetic acid and 2.5 g of silver nitrate, which are dissolved in 40 ml of H$_2$O, are added. Subsequently are further added 50 g of kieselguhr and the mixture evaporated to dryness in vacuo while stirring at 60° to 70° C.

The residue is subsequently reduced at 200° C under a hydrogen atmosphere and the resulting gray-black powder washed with water until no more barium can be detected. Then another drying step is carried out, hydrogen is conducted on top for another hour at 200° C and the powder is allowed to cool under nitrogen.

5 g of the thus prepared catalyst, which contains 11.7 % of palladium, 2.5 % of silver and about 2 % of gold, are introduced into a shaking autoclave together with 58 g of maleic acid (0.5 mole) and 100 g of γ-butyrolactone as solvent. Hydrogen is forced in until the pressure reaches 210 bars, then the temperature is quickly brought up to 235° C and the mixture allowed to react for 5 hours. The catalyst is then removed by centrifugation and the residual reaction solution clear as water (159 g) submitted to analysis. It contains, besides water, γ-butyrolactone (89.7 %) only, corresponding to a yield of about 99 mol % of newly formed γ-butyrolactone. Tetrahydrofurane can be detected in gaschromatographical traces only. No traces can be detected of maleic acid which has not participated in the reaction.

EXAMPLE 4

7.5 g of palladium-(II)-acetate and 9.7 g of platinum-(II)-acetate are dissolved in 400 ml of acetic acid at 70° C. A solution of 2.5 g of silver nitrate in 40 ml of water is added. 50 g of kieselguhr having a specific surface of 0.98 g/m$^2$ are then introduced while stirring, and the result is mixed thoroughly. While continuing agitation, evaporation to dryness is carried out in vacuo at 60° to 70° C and reduction takes place at 200° C for about 2 ½ hours under a hydrogen atmosphere.

5 g of the thus produced catalyst which contains about 5.7 % of palladium, about 9.8 % of platinum and 2.6 % of silver as metals, are introduced into a high-pressure autoclave together with a mixture of 49 g of maleic acid anhydride, 25 g of succinic acid anhydride and 29 g of fumaric acid and 200 ml of dioxane.

Hydrogen is forced in until a pressure of 189 bar is reached, quick heating to 220° C takes place, and reaction is then allowed for about 5 to 6 hours.

The reaction mixture is then cooled and separated from the catalyst by centrifugation. 309 g of a solution clear as water are obtained which contains 27.1 % (83.8 g) of γ-butyrolactone, corresponding to a yield of 97.5 mol %. Only traces (less than 0.1 %) of tetrahydrofurane can be detected.

EXAMPLE 5

15 g of palladium-(II)-acetate and 5 g of silver acetate are introduced into a one-liter-high-pressure-shaking autoclave together with 50 g of kieselguhr, 49 g of maleic acid anhydride and 100 g of tetrahydrofurane. Hydrogen is forced in until a pressure of 208 bars is reached, and quickly heated to 225° C. The reaction is interrupted after 5 hours and quickly cooled.

The liquid reaction product is filtered off the catalyst material and subjected to analysis.

148 g of filtered off reaction solution are obtained, which contains 23.4 % (34.5 g) of γ-butyrolactone, corresponding to a yield of 80.5 mol % of γ-butyrolactone.

This example embodiment, in contrast to the aforesaid examples, provides for preparing the catalyst in situ, i.e. the catalyst is not reduced prior to reaction.

What is claimed is:

1. A process for the manufacture of γ-butyrolactone by catalytic hydrogenation which comprises reacting maleic acid, maleic acid anhydride, succinic acid, succinic acid anhydride, fumaric acid, or a combination thereof, with hydrogen in the presence of a hydrogenation catalyst which contains one or more materials selected from the group consisting of silver, gold and the compounds thereof and a material selected from the group consisting of ruthenium, rhodium, palladium, osmium, iridium, platinum, and the compounds thereof.

2. The process as defined in claim 1 which comprises reaction in the presence of an inert solvent.

3. The process as defined in claim 1, wherein the catalyst contains palladium or a compound thereof.

4. The process as defined in claim 1, wherein the compounds are oxides, oxide-hydrates, carboxylates, chelates of 1,3-diketocompounds, nitrates, carbonates, or oxides, and in the case of gold, also aurates or acetoaurates.

5. The process as defined in claim 1, wherein the catalyst is on a carrier.

6. The process as defined in claim 5, wherein the carrier is silicic dioxide, diatomaceous earth, kieselguhr, silicic-dioxide-aluminum oxide, coal, titanium dioxide, thorium oxide, zircon oxide, silicic carbide, a spinel or aluminum oxide.

7. The process as defined in claim 6, wherein the carrier has a specific surface area of 0.1 to 10 m$^2$/g.

8. The process as defined in claiam 5, wherein the quantity of catalyst is 0.1 to 50 weight % of the total mass of the catalyst and the carrier.

9. The process as defined in claim 1, wherein the weight ratio of the gold or a compound thereof, silver or a compound thereof, or a mixture thereof, to the material selected from the group consisting of ruthenium, rhodium, palladium, osmium, iridium, platinum, and the compounds thereof, calculated on the elements, is of from 99:1 to 1:99.

10. The process as defined in claim 9, wherein the weight ratio is from 10:1 to 1:10.

11. The process as defined in claim 1, wherein reaction is at a temperature of from 50° to 300° C.

12. The process as defined in claim 1, wherein reaction is at a pressure of from 50 to 500 bars.

13. The process as defined in claim 5, wherein the reaction is in the presence of a palladium-silver-catalyst, a palladium-gold-catalyst, or a mixture thereof, and the catalyst is produced by applying onto a carrier a carboxylic acid solution of a palladium-carboxylate or a palladium compound which converts to a carboxylate in the presence of a carboxylic acid together with a gold compound, a silver compound or a mixture thereof, which converts to a carboxylate, by removing the carboxylic acid via a drying step at an elevated temperature in vacuo or at normal pressure and by treating the catalyst in the gaseous or liquid phase with reducing agents at a temperature of from 15° to 200° C.

14. The process as defined in claim 13, wherein the carboxylic acid is an aliphatic carboxylic acid of from 2 to 10 carbon atoms which is liquid under normal conditions and vaporizable without dissociation in vacuo.

15. The process as defined in claim 1, wherein the quantity of catalyst is of from 0.5 to 25 weight %, calculated on the quantity of reactants used for the hydrogenation.

16. The process as defined in claim 3, wherein the catalyst contains palladium or a compound thereof and silver or a compound thereof.

17. The process as defined in claim 3, wherein the catalyst contains palladium or a compound thereof and gold or a compound thereof.

* * * * *